(12) United States Patent  
Gehring

(10) Patent No.: US 9,109,996 B2
(45) Date of Patent: Aug. 18, 2015

(54) MEASURING DEVICE COMPRISING A RESONATOR HAVING A FILM CARRIER

(75) Inventor: Frank K. Gehring, Obernheim (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 296 days.

(21) Appl. No.: 13/636,337

(22) PCT Filed: Mar. 23, 2011

(86) PCT No.: PCT/EP2011/054492
§ 371 (c)(1),
(2), (4) Date: Oct. 15, 2012

(87) PCT Pub. No.: WO2011/117318
PCT Pub. Date: Sep. 29, 2011

(65) Prior Publication Data
US 2013/0125629 A1      May 23, 2013

(30) Foreign Application Priority Data

Mar. 23, 2010 (DE) .......................... 10 2010 016 102

(51) Int. Cl.
| | |
|---|---|
| *G01N 29/02* | (2006.01) |
| *G01N 11/16* | (2006.01) |
| *G01N 29/036* | (2006.01) |
| *G01N 29/22* | (2006.01) |

(52) U.S. Cl.
CPC .............. *G01N 29/022* (2013.01); *G01N 11/16* (2013.01); *G01N 29/036* (2013.01); *G01N 29/222* (2013.01); *G01N 29/226* (2013.01); *G01N 2291/0426* (2013.01)

(58) Field of Classification Search
CPC .... G01N 11/16; G01N 15/1056; G01H 11/08
See application file for complete search history.

(56) References Cited

U.S. PATENT DOCUMENTS

| | | | |
|---|---|---|---|
| 2008/0134767 A1 | 6/2008 | Wakamatsu et al. | |
| 2009/0173158 A1 | 7/2009 | Gehring | |

FOREIGN PATENT DOCUMENTS

| | | |
|---|---|---|
| CN | 101080624 A | 11/2007 |
| DE | 3312923 A1 | 10/1984 |
| DE | 3486221 T2 | 1/1994 |
| DE | 4334834 A1 | 4/1995 |
| DE | 60113846 T2 | 4/2006 |
| DE | 102006015512 A1 | 10/2007 |
| DE | 202009007108 U1 | 9/2009 |
| EP | 1830169 A1 | 9/2007 |
| JP | 2006194866 | 7/2006 |

(Continued)

OTHER PUBLICATIONS

German Patent and Trademark Office, German Office Action Dated Apr. 25, 2013, pp. 1-6, Munich, Germany, Application No. 102010016102.0, Applicant: Andreas Hettich GmbH & Co. KG.

(Continued)

*Primary Examiner* — Paul West
(74) *Attorney, Agent, or Firm* — Woodling, Krost and Rust

(57) ABSTRACT

The invention relates to a measuring device (10, 50) comprising a resonator (20, 52) having a sensitive) being inserted in the region and a base support unit (26, 30) for measuring properties of a fluid, the resonator (20, 52base support unit (26, 30) and contacted therein, the sensitive region remaining accessible to the fluid, and the resonator (20, 52) being activatable via connection points (24, 40) on the base support unit (26, 30). The invention is characterized in that the base support unit (26, 30) is formed solely by a film arrangement.

4 Claims, 3 Drawing Sheets

(56) References Cited

FOREIGN PATENT DOCUMENTS

| JP | 2006194867 | | 7/2006 |
|----|------------|----|--------|
| JP | 2008502911 | | 1/2008 |
| JP | 2009531678 | | 9/2009 |
| WO | 2007085353 | A1 | 8/2007 |
| WO | 2009153063 | | 12/2009 |
| WO | 2009153063 | A1 | 12/2009 |

OTHER PUBLICATIONS

The State Intellectual Property Office of P.R. China, Office Action, Dec. 24, 2013, Application No. 201180015259.8, Applicant: Andreas Hettich GmbH &Co. KG, pp. 1-7, P.R. China.

The State Intellectual Property Office of P.R. China, English Translation of Office Action, Dec. 24, 2013, Application No. 201180015259.8, Applicant: Andreas Hettich &Co. KG, pp. 1-9, P.R. China.

Japan Patent Office, Office Action, January 14, 2014, Japanese Patent Application No. 2013-500502, pp. 1-2, Japan.

Japan Patent Office, English Translation of Office Action, Jan. 14, 2014, Japanese Patent Application No. 2013-500502, pp. 1-2, Japan.

International Search Report, European Patent Office, May 30, 2011, International Application No. PCT/EP211/054492, pp. 1-4.

PCT/EP2011/054492, International Preliminary Report on Patentability, Written Opinion of the International Searching Authority, The International Bureau of WIPO, Sep. 25, 2012, Applicant Andreas Hettich GmbH & Co. KG.

MEASURING DEVICE COMPRISING A RESONATOR HAVING A FILM CARRIER

This application is the national phase entry of PCT/EP2011/054492. This application claims the benefit and priority of and to PCT/EP2011/054492, international application filing date Mar. 23, 2011, which claims the benefit and priority of and to German patent application no. DE 10 2010 016 102.0, filed Mar. 23, 2010. PCT/EP2011/054492, international application filing date Mar. 23, 2011, and German patent application no. DE 10 2010 016 102.0, filed Mar. 23, 2010, are incorporated herein by reference hereto.

The invention relates to a measuring device comprising a resonator and a handpiece for accommodating the measuring device.

Known from the closest prior art, i.e. DE 10 2006 015 512 A1, is an oscillating quartz crystal for analysing fluids. For this purpose, the oscillating quartz crystal has a sensitive region on the measuring surface. For ease of handling and for sealing, the oscillating quartz crystal has its measuring surface connected to a film. This film has an opening which gives access to a sensitive region of the oscillating quartz crystal. This film is glued to the upper edge of the oscillating quartz crystal in general. This arrangement, together with the film, is inserted into a base support unit, with contacts being provided on the support means for contacting the oscillating quartz crystal. Said contacting is accomplished by placing a measuring chamber onto said film which will press the quartz crystal against the contacts provided in the support means. However, the disadvantage of this arrangement is that due to the necessity of applying force onto said quartz crystal from the outside, it will always have to involve some device. Such a device will mechanically fix the quartz crystal/film arrangement in place which will automatically result in a dead volume to be created above the sensor surface.

Similarly designed is an immersion probe as disclosed in DE 20 2009 007 108 U1. In this invention, an oscillating quartz crystal is inserted into a sensor head in such a manner that it will rest on the edge region of the housing. The sensitive area of the oscillating quartz crystal is sealed by means of an O-ring which also fixes the oscillating quartz crystal in place. In this embodiment, the use of this O-ring also results in an open-topped measuring chamber which in turn causes a dead volume to be formed. Moreover, due to the relatively large dimensions of the sensor head, its design only allows immersion into relatively large vessels.

Known from US 2008/0134767 A1 is a resonator which can be connected to a rigid circuit board via a quartz carrier. A lid encompasses the quartz carrier, the resonator and the circuit board and holds everything together through non-positive and positive form locking.

It is the object of the present invention to provide a measuring device which only requires a very small installation space and can be used on its own. Furthermore, said measuring device should be capable of being used flexibly and should not exhibit any dead volume above its sensitive sensor surface.

In a known manner, the measuring device comprises a base support unit with connection points via which a resonator can be contacted and thus activated and evaluated.

According to the invention, the base support unit is merely formed by a film arrangement, with the resonator being mounted in a spaced position from the lower film to allow said resonator to oscillate largely undamped.

The film arrangement has the advantage that it makes processing and assembly of the individual components, in particular the films, very easy and accordingly inexpensive. Individual films can be provided in a simple manner as their processing merely involves cutting out and/or taking out individual film portions and connecting the individual films. This allows a precise detecting means to be provided in the form of a disposable article.

According to another inventive principle the resonator has one surface thereof, which also exhibits the sensitive area, connected to a final film. Said final film fixes the resonator in its position in the base support unit and tensions it so as to ensure electrical contacting. The final film is attached to the resonator in a fluid-tight manner and includes an opening for access to the sensitive area of the resonator. The fact that the final film tensions the resonator and fixes it in position ensures that the resonator is held in a contacted position and allows dead-volume-free measurements to be performed at the sensitive area as very little material is added by the final film. Furthermore, the resonator is only minimally pre-tensioned which clearly improves the measuring results.

In an advantageous embodiment, the support unit comprises a bottom film which delimits the support unit toward the bottom and seals the oscillating quartz crystal toward the bottom.

In particular, conductor paths may be provided on the bottom film which end in resonator contact pads. For contacting, the resonator will then be fitted onto these conductor paths which are preferably of a thickness such that the contact pads will keep the fitted resonator spaced from the bottom film.

Preferably, however, a support film is additionally provided on said bottom film. This support film is designed such that the resonator fitted onto the support film will only rest upon the latter at the edges. The support film helps keeping the resonator spaced at a certain distance from the bottom film. To be more specific, the resonator contact pads are provided on the support film. Accordingly, the conductor paths are also provided on the support film.

In yet another preferred embodiment, a spacer film may be provided above said support film. This spacer film has an opening through which the resonator may be fitted onto the support film or also the bottom film. The diameter of said opening may preferably be chosen to be slightly larger than the diameter of the resonator to be fitted therethrough to allow it to oscillate freely in the lateral direction. This design has the advantage that it prevents a short circuit as only one electrode of the resonator can be accessed through this opening.

The spacer film allows compensating for the thickness of the resonator. Consequently, the base support unit may be designed such that its upper surface is almost flush with the resonator surface. As a result, the resonator may be held in place using only some pre-tensioning and/or tightening. In particular, the spacer film has a thickness such that its upper surface is spaced approx. 50 µm relative to the resonator surface. The thickness of the spacer film can be calculated to be $d=(c/f)/2-x$, with c being the speed of sound, f the resonant frequency of the resonator and x the difference in height as a function of the desired pre-tension. For a resulting thickness $d<=0$ no spacer film will be required.

The term film as used in this invention not only refers to polymer films exclusively but merely to layers of very low thicknesses, preferably in the order of micrometers.

The resonator can be made to contact a fluid for analysis thereof and responds to a mass deposition of the material, substance, particles and/or microorganisms to be detected by a change in the resonant frequency and/or damping. Such may then be evaluated via an associated measuring unit.

On its measuring surface having the sensitive region, the resonator may exhibit a first electrode which covers the entire resonator surface. This electrode extends beyond the resonator edge and onto the bottom side of the quartz crystal where it features a contact pad for contacting one of the two conductor paths. Moreover, the bottom side of the quartz crystal is provided with another electrode which does not cover the entire surface of the bottom side and is thus electrically separated from the first electrode and connected to the other one of the two conductor paths.

For sealing the oscillating quartz crystal, an adhesive layer may be applied between the measuring surface of the resonator and the base support unit. Moreover, such layer will fix the oscillating quartz crystal in position on the contact pads.

As an alternative to an adhesive connection, a final film may also be used which is placed on the upper side of the oscillating quartz crystal in such a manner that the sensitive region of the oscillating quartz crystal will still be accessible and extends at least partially over the base support unit and is connected thereto.

In particular, the resonator is not glued to the base support unit or the final film but is held in place merely by the tension created by the final film. This has the advantage that it clearly simplifies its manufacture since no adhesive has to be applied to the resonator itself as this always involves the danger of contaminating the resonator surface. Furthermore, supporting the resonator solely through pre-tensioning has a beneficial effect on the oscillating behaviour of the resonator as the latter will be able to oscillate freely in a lateral direction.

Preferably, the final film may be attached to the base support unit by means of a thermal adhesive connection. This facilitates production since no separate adhesive will have to be applied.

In that the resonator is not directly glued to the base support unit but is held in position by the pre-tensioning of the final film above it, the resonator is mechanically detached to a certain extent. If the support structure, for example its area of connection, is bent, this will merely have a negligible adverse effect on the resonator's vibration characteristics.

As the final film is of a very small thickness compared to the diameter of the resonator, contrary to the prior art, no measuring space will be created at the surface which will result in a dead volume. This likewise prevents the formation of air bubbles above the sensor surface which would make it impossible to measure adsorption.

To be more specific, the final film has a diameter of its opening which is slightly smaller than the diameter of the resonator. Consequently, the film will only rest on the edge region where the smallest vibration amplitudes occur. As a result, damping of the resonator by the final film will be minimal.

The film layers may be interconnected by means of adhesives. Preferably, the adhesive bond may be in the form of a thermal adhesive bond. This allows the individual components of the arrangement to be aligned precisely and to be glued to each other under the influence of thermal energy.

To be more specific, the support film is provided in the form of a ceramic film. On the one hand, this ensures a certain degree of stability, on the other hand it allows further processing by means of evaporation deposition. Moreover, conductor paths are provided which will provide contact to the resonator when the latter is pressed onto the conductor path. The conductor paths may preferably be mounted on the support film. As the resonator is spaced from the film through the conductor paths, stresses are avoided and easy contacting of the resonator is possible. Preferably, the contact points on the film are made of gold.

In a particularly advantageous embodiment, all films are made of polyimide (PI). Making the arrangement basically flexible through the use of film of a low rigidity has the advantage that the film arrangement will not be prone to breaking.

Furthermore, the film arrangement may be stiffened in the region of the resonator by means of a thicker film. This will increase the quality of the measuring result obtained since this clearly reduces the introduced stresses.

Providing the base support unit as a film arrangement has the advantage that after one measurement, the entire support unit may be disposed of. This is especially advantageous as it guarantees that the resonator will not be contaminated, with a view to subsequent measurements. This simple exchangeability is accomplished in that the design according to the invention is an inexpensive implementation of a measuring device comprising a resonator.

The base support unit exhibits the required contact points on one surface thereof. The contact points are provided in the form of circuit board contact pads. These may preferably be provided on the support film. Where a carrier film or even a final film is provided above the support film, these films have openings in the region of the circuit board contact pads through which the circuit board contact pads can be accessed. The circuit board contact pads may preferably be flat and thin opposite the conductor paths provided there.

Via the circuit board contact pads, the oscillating quartz crystal can readily be accessed and easily be contacted with clamping or spring contacts. This allows the most varied applications. For example, the measuring device may simply be contacted with a probe station having probe tips and the sample fluid to be analysed may be pipeted onto the resonator. This allows its use in connection with common lab equipment which makes this arrangement especially interesting for single tests.

The films may each be of a thickness of between 25 μm and 100 μm, in particular 50 μm, and are connected by means of adhesive layers of approx. 18 μm in thickness. Consequently, the total thickness of the measuring device is extremely small. This very thin design of the support unit accommodating the oscillating quartz crystal allows the measuring device to be used in various applications, even in the smallest vessels containing the smallest sample volumes.

Besides the analysis of the vibration parameters of the resonator, the measuring device may also be used as a working electrode for electro-chemical measurements.

In a particularly advantageous embodiment, the support unit is rounded in a semicircular shape along the circumference of the oscillating quartz crystal. This allows the oscillating quartz crystal, when used in an immersion probe, to be moved as close to the bottom of the vessel as possible in order to keep the required measuring volume as small as possible. Especially with expensive fluid samples, this offers a vast cost savings potential.

According to yet another embodiment, a handpiece is provided in which the circuit-board-like measuring unit may be inserted. Consequently, the handpiece, at a first end thereof, includes accommodation and contact means for the circuit-board-like measuring device or support unit.

In one embodiment, the measuring device is fixed in its position within the accommodation means and projects from the handpiece. This guarantees minimum dimensions, thus allowing it to also be used in small amounts of liquid samples. In this configuration, the oscillating crystal quartz may also be used as an immersion probe for detecting and/or measuring the concentration of materials, substances and/or microorganisms in fluids.

The accommodation means may be provided with a lateral guide which guides the support unit laterally. Contacting is achieved through a spring clip. To be more precise, this spring clip is designed in two parts, with the two clip contacts being connected via an insulator. This holds the two ends stable relative to each other and allows them to be moved at the same time in order to ensure the insertion of the measuring device. This embodiment has the advantage that the same clamp can be used to achieve both a mechanical fixation in place and the electrical contacting of the circuit-board contact pads. More specifically, the clamp which is introduced into the housing is sealed against moisture, which may for example be achieved by sealing the housing with silicone. Furthermore, the ends of the clamp are made to extend to a connection circuit board within said housing and soldered thereto.

In yet another embodiment, the handpiece is of the two-part design. In a first component thereof, the cables or further electronics may be accommodated. The second component, at a free end thereof, exhibits accommodation means for the measuring device and, at another end thereof, a contact and connection circuit board for connection to the first component of the handpiece. The second component is coupled to the first component of the handpiece in such a way that the inner space of the first component is protected from moisture. Accordingly, the two components may be sealed from each other through a seal ring. Preferably the components of the handpiece overlap in the transition area. As a result, the connection circuit board which is located in the second component also extends within the first component.

In addition, the handpiece may exhibit a connector which allows it to be connected to a voltage supply and/or to evaluation devices. This connector is especially provided in the form of a BNC connector.

Following below is a more detailed description of the invention with reference to the drawings. Further details and advantages that are essential to the invention may be gathered from the drawings and their descriptions. The reference numerals used throughout the drawings are as listed in the list of reference numerals.

Figure 1:
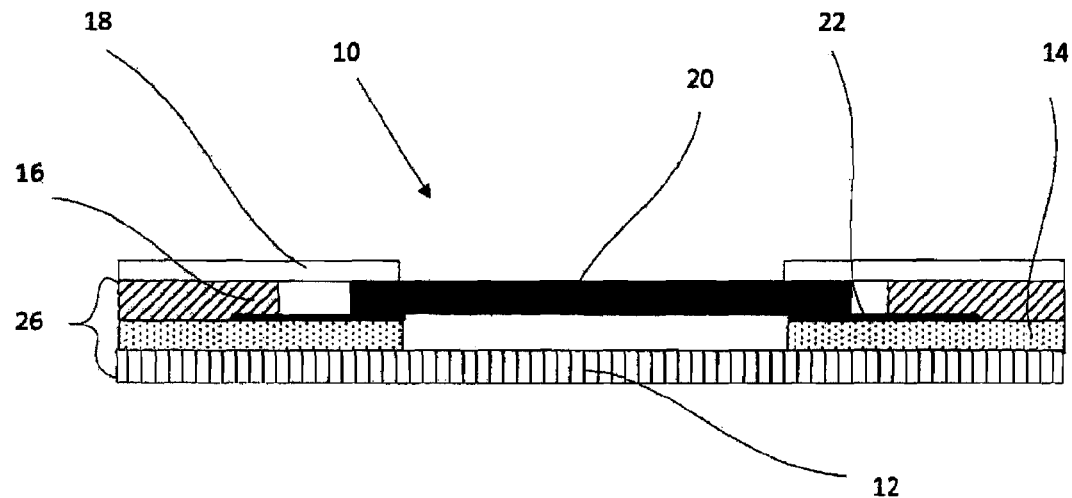
FIG. 1 is a cross-sectional view of the resonator circuit board.

FIG. 1 is a cross-sectional view of a resonator circuit board 10. Said resonator circuit board 10 comprises a base support unit consisting of a bottom film 12, a support film 14 and a spacer film 16. Moreover, a final film 18 is provided which fixes the oscillating quartz crystal 20 in its position within the base support unit. In addition, the support film 14 includes conductor paths 22. These conductor paths end in resonator contacts 22 at the edge of the oscillating quartz crystal.

For the formation of the base support unit 26, a support film 14 is glued onto the bottom film 12. The support film 14 is provided with resonator contacts 22 on its upper side. The resonator 20, which likewise exhibits contacts for its electrodes at its bottom side, rests on the resonator contacts 22 via those contacts. In order to fix the resonator 20 in place, it has its upper side, which also includes the sensitive element of the resonator, glued to a final film 18 which merely rests on the edge region of the resonator 20. The spacer film 16 is of a thickness that will ensure that the final film 18 glued to it will exert as little pressure as possible on the resonator 20. Still, the pressure exerted will be sufficiently large to permanently and reliably electrically connect the contact surfaces of the resonator 20 to the resonator contacts 22. This arrangement creates a resonator circuit board in a simple way which can be flexibly and readily used owing to its dimensions and the contact points provided thereon. Moreover, owing to its inexpensive design, it can also be used as a disposable article. This is particularly useful for measurements for which the possibility of contamination has to be ruled out completely.

Figure 2:
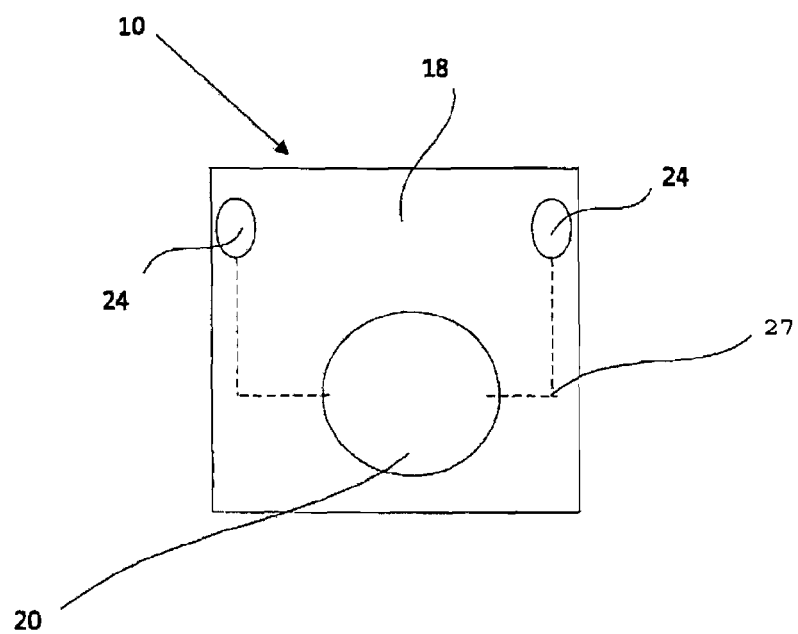
FIG. 2 is a top view of a resonator circuit board.

FIG. 2 is a schematic top view of a resonator circuit board 10 according to FIG. 1. The resonator circuit board 10 is substantially square in shape and is delimited toward the top by the final film 18. Furthermore, the sensitive region of the resonator 20 is shown therein. The quartz contact points 22 deposited on the support film as well as the conductor paths 27 are merely indicated in the view. The conductor paths 27 connect the quartz contacts 22 to the connector contacts 24. The connector contacts 24 are accessible from the outside via openings in the final film 18.

Thus the resonator 20 may be contacted and activated by conventional measuring and control devices via the easily accessible connector contacts 24 in a simple manner without the need for complex chamber designs.

Figure 3:
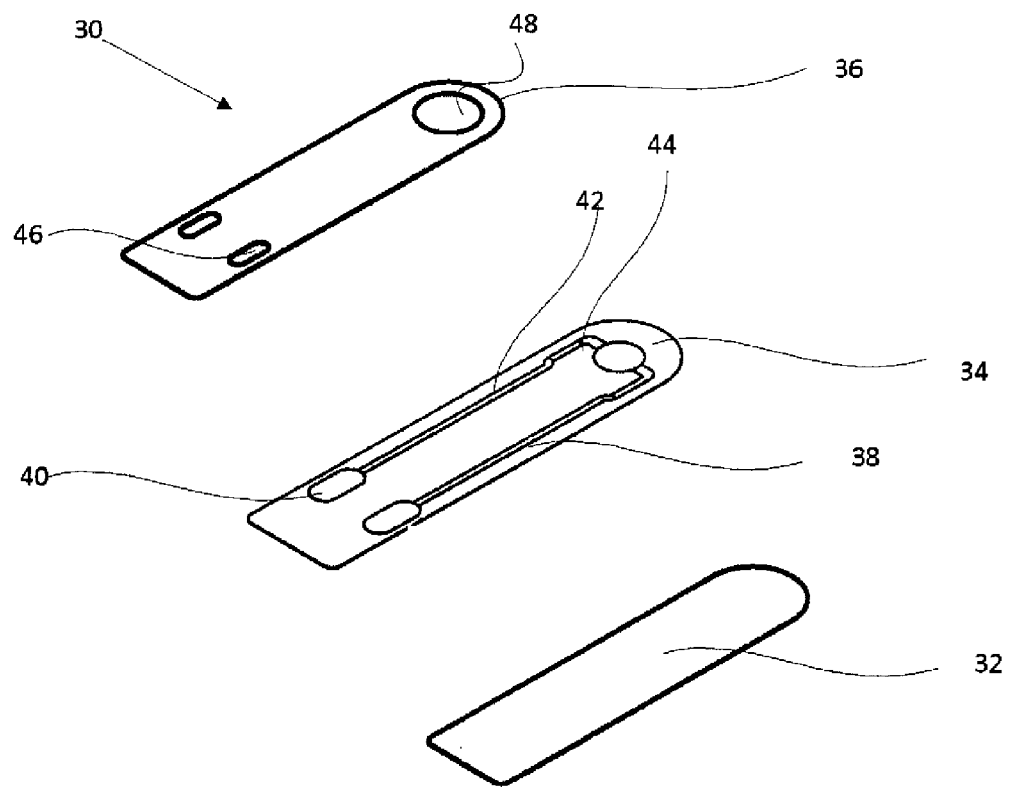
FIG. 3 is a view of the base support unit of a support unit which is composed of three films.

FIG. 3 is a view of the base support unit 30 which consists of three films, a bottom film 32, a support film 34 and a final film 36. The centrepiece of the base support unit 30 is constituted by the support film 34. The latter has quartz contact points 44 which are connected to the connector contacts 40 via a conductor path 42. Connector contact and quartz contact points 44 are chemically gold-plated and have a thickness of approx. 1 to 2 micrometers. The two contact points are connected to a copper conductor path which is approx. 35 micrometers thick. For forming the base support unit 30, the bottom film 32, the support film 34 and the spacer film 36 are glued together with a silicone-containing acrylic adhesive. The adhesive layer is deposited to a thickness of approx. 25 micrometers.

Figure 4:
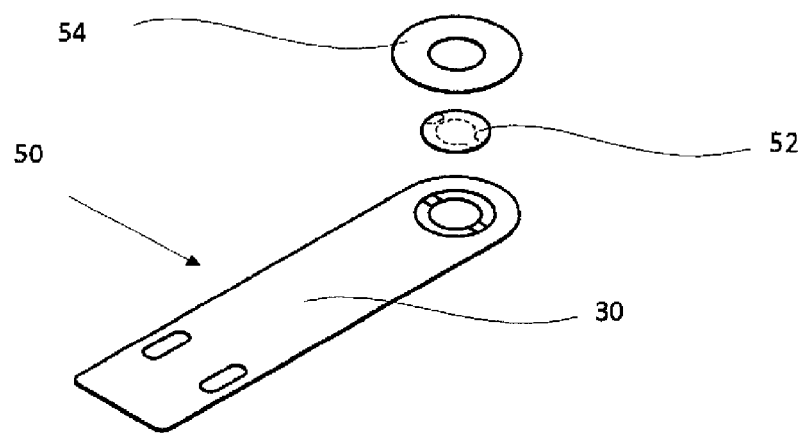
FIG. 4 is a view of the base support unit having an oscillating quartz crystal and a final film.

FIG. 4 shows a resonator circuit board 50 comprising the base support unit 30 and a final film 54. For obtaining the measuring device, the resonator 52 is inserted into the opening provided in the base support unit 30 and glued there by means of the final film 54. The final film 54 merely rests on the edges of the resonator 52. The final film 54 seals the sensitive resonator surface from the rest of the resonator 52. This also maintains the circumferential distance of the resonator 52 from the spacer film and the resonator can oscillate freely. Via the base support unit 30 and the final film 54, the front portion of the support unit 50 is completely sealed from any fluid penetration. This makes this arrangement also especially suited for use as an immersion probe.

Figure 5:
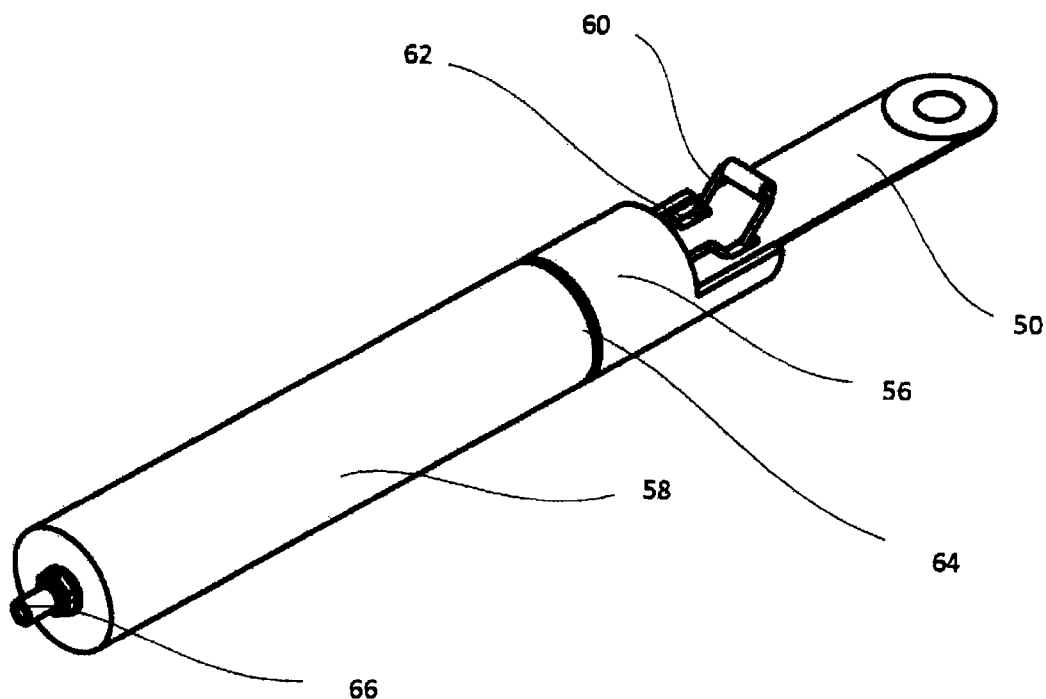
FIG. 5 is a view of the handpiece with the resonator circuit board inserted therein.

FIG. 5 is a view of the resonator circuit board 50 as inserted into a two-part handpiece comprising a first component 56 and a second component 58. For accommodating the support unit 50, the front end is provided with a contact clamp 60 which engages the contact points 62, makes contact with the handpiece via these and at the same time fixes the support unit 50 in position via its spring effect. The first handpiece component 56 and the second handpiece component 58 are connected to each other via a seal ring 64. This prevents fluid or moisture from entering the second handpiece component. Disposed on the distal end of the second handpiece component is a BNC connector 66 which can be used to connect it to the power supply and the measuring device.

This configuration is especially suited for use as an immersion probe as it allows the measuring device to be positioned as desired owing to the fact that it is movably supported within the handpiece, and can thus also be immersed in a vessel containing a sample fluid. The handpiece components are made of PEEK as PEEK is particularly resistant to chemicals and temperature and also constitutes an electrical insulator. Moreover, the handpiece, in particular its second component, may be used as a support for additional electrical signal processing means or other circuitry.

This tremendously increases the range of possible applications of the measuring device according to the invention.

Figure 6:
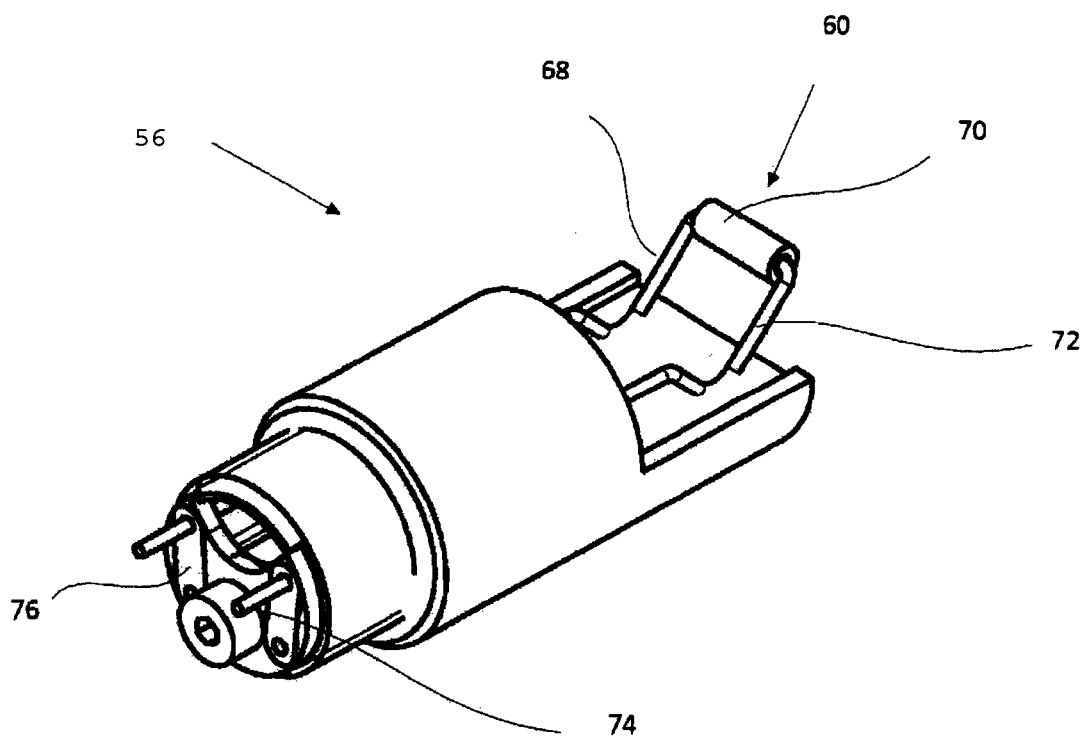
FIG. 6 is a detailed view of a first component of the handpiece.

FIG. 6 is a detailed view of the second handpiece component 52. What should be particularly noted here is the contact clamp 60 which consists of a first contact 69 and a second contact 72 which are interconnected via a mounting insulator 70. The distal ends of the contacts 69, 72 are accommodated in the first component of the handpiece. Moreover, they have their accommodating ends shaped such that the contacts 68, 72 will exert a spring load on the contact surface of the second component of the hand piece. In addition, the accommodating means includes a lateral guide for adjustment of the measuring device of the resonator circuit board. The ends of the contacts 68, 72 are housed in a contact circuit board 76. The latter will increase the conducting contact so as to ensure a safe and secure contact between the first and second handpiece components. The insulator 70 connecting the two contacts 68, 72 has the additional advantage that it not only electrically separates and mechanically connects the two contacts but also serves as a control element for the connection of a resonator circuit board, owing to the special shape of the contacts. The insulator 70 is easily accessible and can thus be reached and lifted without any problem.

LIST OF REFERENCE SIGNS 10 resonator circuit board
12 bottom film
14 support film
16 spacer film
18 final film
20 resonator
22 contacts
24 connector contact
26 base support unit
27 conductors
30 base support unit
32 bottom film
34 support film
36 spacer film
38 conductor path
40 connector contact
42 conductor path
44 quartz crystal contact point
46 contact opening
48 quartz crystal opening
50 resonator circuit board
52 resonator
54 final film
56 first handpiece component
58 second handpiece component
60 contact clamp
62 resonator circuit board contact
64 seal
66 BNC connector
68 first contact
70 insulator connection
72 second contact
74 component contact
76 contact circuit board

The invention claimed is:

1. A measuring device (10, 50), comprising:
a base support unit (26, 30);
said base support unit comprises a film arrangement;
said film arrangement includes a bottom film, a support film, a spacer film and a final film;
a resonator (20, 52), said resonator includes a periphery;
said bottom film affixed to said support film, and said spacer film affixed to said support film;
said support film includes electrical contacts, electrical conductor paths (27, 42) and electrical connection points (24, 40);
an electrical source for engagement with said electrical connection points;
said electrical conductor paths (22, 42) in electrical communication with said electrical contacts and said electrical connection points (24, 40) of said support film;
said resonator includes a sensitive region for measuring properties of a fluid, and, said sensitive region of said resonator accessible to said fluid;
said resonator includes electrical contacts;
said electrical contacts of said resonator engage said electrical contacts of said support film, and thus, said electrical contacts of said resonator are in electrical communication with said electrical connection points via said electrical conductor paths (22, 42);
said spacer film includes a first opening therein and said resonator resides within said first opening of said spacer film;
said final film includes a second opening therein, and, said final film engages said spacer film and said periphery of said resonator;
said final film includes a third opening and a fourth opening, said third opening aligned with one of said electrical connection points and said fourth opening aligning with the other electrical connection points, said third and fourth openings of said final film enabling engagement of said electrical source with said connection points for activation of said resonator (20, 52).

2. The measuring device (10, 50) according to claim 1 wherein said resonator is suspended across said spacer film and underdamped.

3. The measuring device (10, 50) according to claim 1, wherein said final film tensions said resonator to ensure electrical contact with said electrical contacts of said support film.

4. The measuring device (10, 50) according to claims 1 wherein said bottom film, said support film, said spacer film, and said final film are polyimide.

* * * * *

UNITED STATES PATENT AND TRADEMARK OFFICE
CERTIFICATE OF CORRECTION

| | |
|---|---|
| PATENT NO. | : 9,109,996 B2 |
| APPLICATION NO. | : 13/636337 |
| DATED | : August 18, 2015 |
| INVENTOR(S) | : Gehring |

Page 1 of 1

It is certified that error appears in the above-identified patent and that said Letters Patent is hereby corrected as shown below:

On the title page item (57),

Line 2, abstract, after "sensitive" delete ") being inserted in the".

Line 4, abstract, after "(20, 52" insert -- ) being inserted in the --.

Signed and Sealed this
Thirty-first Day of May, 2016

Michelle K. Lee
*Director of the United States Patent and Trademark Office*